United States Patent [19]
Raoz

[11] Patent Number: 5,993,437
[45] Date of Patent: Nov. 30, 1999

[54] CATHETER CONNECTOR

[75] Inventor: N. Sandor Raoz, Greenfield Center, N.Y.

[73] Assignee: Epimed International, Inc., Gloversville, N.Y.

[21] Appl. No.: 09/007,460

[22] Filed: Jan. 15, 1998

[51] Int. Cl.$^6$ .................................................. A61M 5/00
[52] U.S. Cl. ..................... 604/536; 604/533; 604/905; 128/912
[58] Field of Search .................. 604/30, 32–34, 604/186, 246, 248, 249, 250, 256, 283, 905, 533, 536; 128/912; D24/129; 251/4, 7, 8

[56] References Cited

U.S. PATENT DOCUMENTS

| | | | |
|---|---|---|---|
| 3,920,215 | 11/1975 | Knauf | ............................................ 251/7 |
| 4,323,065 | 4/1982 | Kling . | |
| 4,568,334 | 2/1986 | Lynn . | |
| 4,615,692 | 10/1986 | Giacalone et al. . | |
| 4,769,017 | 9/1988 | Fath et al. . | |
| 4,950,255 | 8/1990 | Brown et al. . | |
| 5,053,015 | 10/1991 | Gross . | |
| 5,167,636 | 12/1992 | Clement | .................................... 604/256 |
| 5,188,607 | 2/1993 | Wu . | |
| 5,234,413 | 8/1993 | Wonder et al. | ........................... 604/248 |
| 5,336,206 | 8/1994 | Shichman | ................................. 604/164 |
| 5,350,364 | 9/1994 | Stephens et al. | ........................ 604/256 |
| 5,390,898 | 2/1995 | Smedley et al. | .......................... 604/256 |
| 5,489,274 | 2/1996 | Chu et al. | ................................. 604/248 |
| 5,505,714 | 4/1996 | Dassa et al. | .............................. 604/256 |
| 5,531,723 | 7/1996 | Solazzo . | |
| 5,556,387 | 9/1996 | Mollenauer et al. | ..................... 604/249 |
| 5,603,702 | 2/1997 | Smith et al. | .............................. 604/256 |
| 5,806,551 | 9/1998 | Meloul et al. | ............................ 604/905 |

Primary Examiner—Wynn Wood Coggins
Assistant Examiner—Sharon Finkel
Attorney, Agent, or Firm—Trask, Britt & Rossa

[57] ABSTRACT

Compressible lock washers for use in catheter connectors. One such lock washer (60) includes a support ring (62) and tube engagement flanges (64) extending centrally therefrom, oblique to the ring and each extending from the same side thereof. The tube engagement flanges (64) define a tube receptacle (72) through which a catheter tube (58) may be inserted. Upon compression of the lock washer (60), the tube engagement flanges (64) are forced toward the ring (62), decreasing the diameter of the tube receptacle (72). Thus, during compression of the lock washer (60), the tube engagement flanges (64) engage the catheter tube (58) which runs through the tube receptacle (72), securing the catheter tube within the catheter connector (20) with which the lock washer is associated.

16 Claims, 4 Drawing Sheets

CATHETER CONNECTOR

TECHNICAL FIELD

This invention generally relates to connectors for catheters which introduce fluids into body cavities. More specifically, the invention relates to devices disposed within catheter connectors which prevent the dislocation of a catheter tube from a catheter connector.

BACKGROUND

Catheter connectors are well known. One such device, which is commonly referred to as a "Tuohy-Borst" connector, includes two threaded members which enclose an elongated, compressible O-ring. In use of that device, a catheter tube is inserted into one of the connector members and inserted through a channel defined by the O-ring. Upon engagement of the two threaded members, the O-ring is longitudinally compressed, decreasing the cross-sectional diameter of the channel and frictionally securing the catheter tube therein.

A similar device is disclosed in U.S. Pat. No. 5,053,015 to Gross (Oct. 1, 1991). The catheter connector of Gross includes a body member, into which a catheter tube is insertable, a compression member which locks onto the body member upon interconnection therewith, and a compressible, elongated plug disposed in the body member. In use of that device, a catheter tube is inserted into the body member and through a channel of the elongated plug. Upon engagement of the body and compression members, the elongated plug is compressed, which decreases the cross-sectional diameter of the channel and frictionally secures the catheter tube therein. The connector assembly of Gross also includes a slip washer, which merely facilitates the rotational interconnection of the body and compression members (i.e., by screwing the complementary threaded body and compression members together).

Such devices are somewhat problematic in that the sole use of a compressible member having a channel formed therethrough may be insufficient to adequately secure a catheter tube within the connector especially if the catheter surface gets wet before insertion of the catheter tube into the connector.

DISCLOSURE OF THE INVENTION

Although the previously-described catheter connectors work well for many applications, it has been found that an additional catheter tube-securing element prevents dislocation of a catheter tube from the catheter connector to an even greater degree.

The invention thus includes a compressible lock washer which is useful in a catheter connector. As the lock washer is compressed, the cross-sectional diameter of a tube receptacle formed centrally therethrough decreases, thus securing a tube placed therein. In use, a catheter tube is inserted into a catheter connector assembly, including the lock washer disposed therein. Upon interconnection of the catheter connector members, the lock washer is compressed, decreasing the cross-sectional diameter of the tube receptacle and engaging the catheter tube which runs therethrough.

In another aspect, the invention includes a catheter connector assembly including a compressible lock washer, as previously described, and methods for manufacturing the lock washer and connector.

BRIEF DESCRIPTION OF THE FIGURES

In the drawings, which depict presently preferred embodiments of the invention and in which like reference numerals refer to like parts in different views.

BEST MODE OF THE INVENTION

Figure 1:
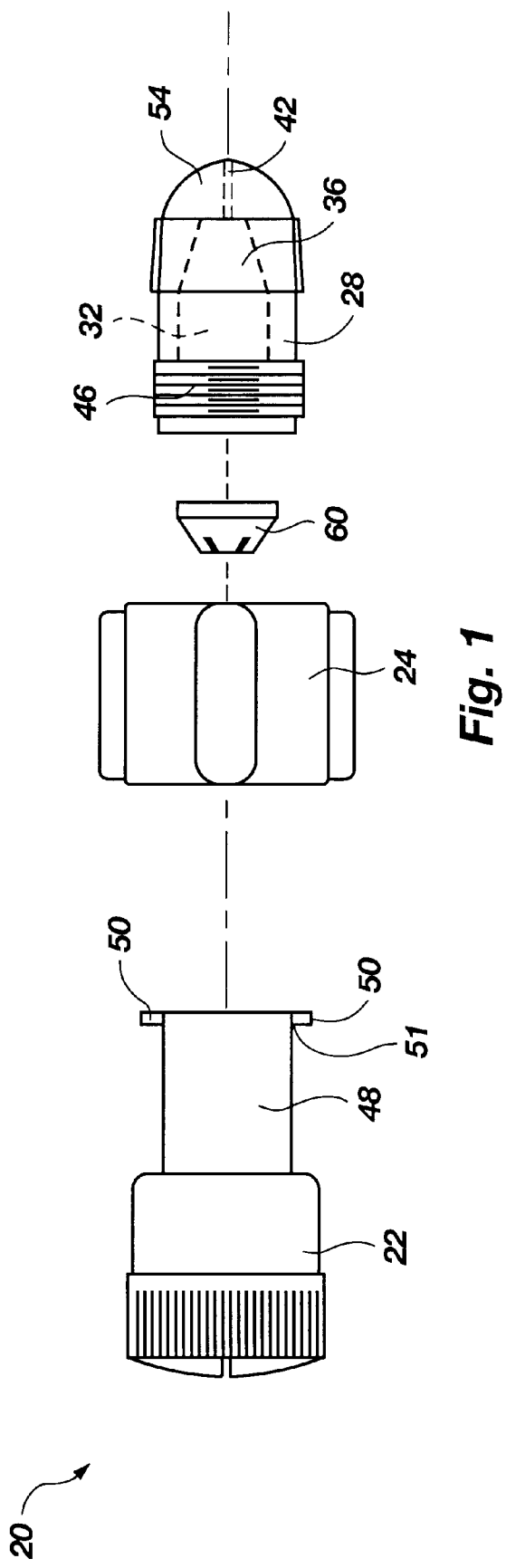
FIG. 1 is an exploded assembly view which depicts an embodiment of a lock washer according to the present invention associated with various catheter connector components.
Figure 11:
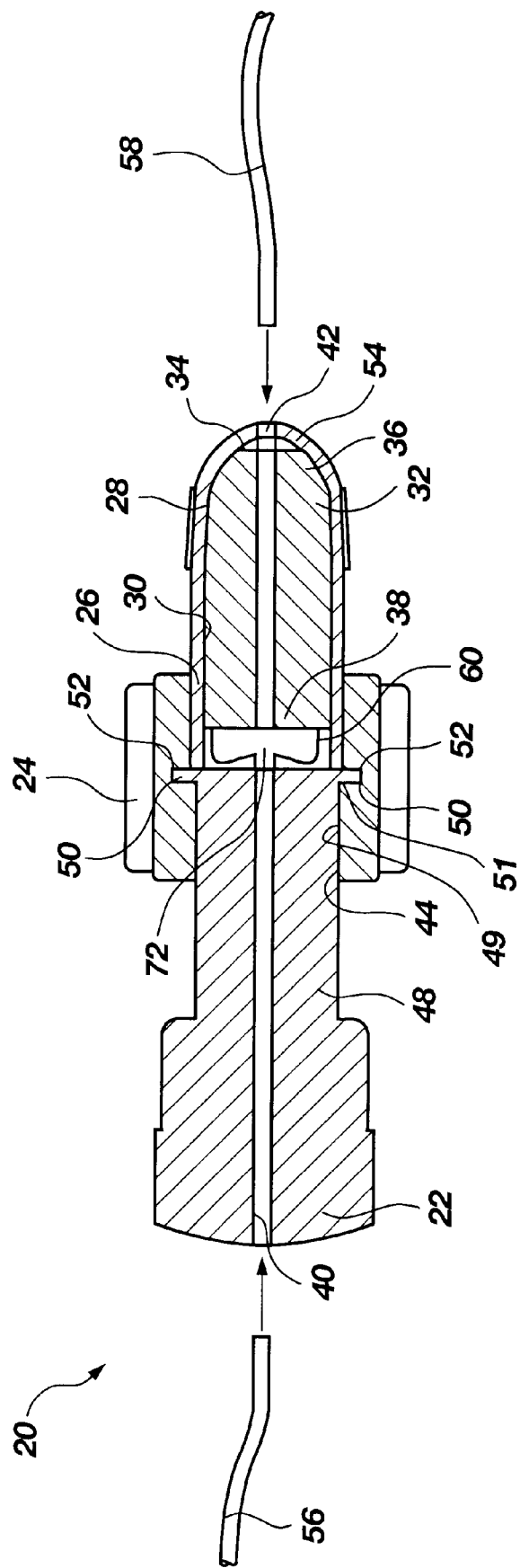
FIG. 11 is a cross-sectional assembly view of a connector assembly which includes a lock washer according to the present invention, illustrating the lock washer in an engaged state.

As shown in FIGS. 1 and 11, a connector lock washer 60 of the present invention is shown in conjunction with a catheter connector generally 20 including a cap 22, a center member 24, an insertion member 28, and a gasket 32.

The distal end of the cap 22 includes a body and may also include an elongated cylindrical extension, which is referred to as an alignment element 48. The body of the cap 22 defines an elongated lumen 40 that is open to the proximal end of the cap and extends approximately centrally through the cap and into the alignment element 48 thereof. The alignment element 48 includes an end wall 56, thus lumen 40 includes a closed end. The cap 22 also includes a center member receptacle 51 formed on the distal end thereof for receiving and engaging the proximal end of the center member 24 (i.e., locking element 49, described below). The center member receptacle 51 includes an interconnect component 50 (e.g., a LEUR LOCK™ extensions) formed thereon.

The center member 24, which is also referred to as a second member for simplicity, is a generally hollow cylindrical member including a body that defines a lumen 44 entirely therethrough. An insertion member receptacle 26 is disposed about the periphery of the center member 24, proximate the distal end of the same. The insertion member receptacle 26 is configured to receive the proximal end of the insertion member 28 and interconnect therewith (e.g., by threads). The proximal end of the center member 24 is referred to as a locking element 49. The proximal end of the lumen 44 is defined by locking element 49 and is configured to receive the alignment element 48 of the cap 22. The cross-sectional diameter of the lumen 44 may decrease near the distal end of the center member 24. The locling element 49 includes locking elements 52 (e.g., LEUR LOCK™ receptacles) adjacent the distal end thereof, which are configured to engage the interconnect component 50 of the cap 22.

The insertion member 28, which is also referred to as a first member for simplicity, is also a generally hollow cylindrical member including a body that defines an elongated lumen 30 through the center thereof, a distal end 54, and a substantially round aperture 42 formed approximately centrally through the distal end. The proximal end of the insertion member 28 includes an interconnection component 46 (e.g., external threading) that is complementary to a first receptacle 26 (which includes, e.g., internal threading) and configured to interconnect therewith. The lumen 30 is configured to receive a gasket 32. The distal end aperture 42 is configured to facilitate the insertion of a catheter tube 58 therethrough.

The lock washer 60 and gasket 32 are disposed within the lumen 30 of the insertion member 28 and are held into place by the interconnection of the insertion member 28 with the center member 24. In order to interconnect the center member 24 and the insertion member 28, the interconnection component 46 of the insertion member 28 is inserted into and engaged by the receptacle 26 of the distal end of the center member 24.

Figure 2:
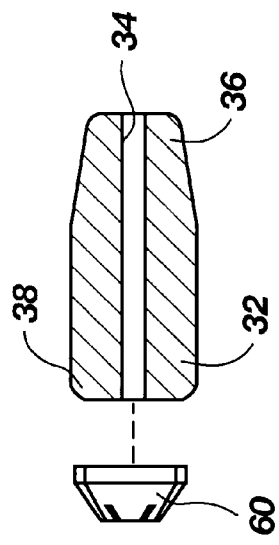
FIG. 2 depicts the embodiment of the preceding figure and its relation to a gasket.

With reference to FIG. 2, a preferred gasket 32 is an elongated, compressible, resilient, somewhat cylindrical element which defmes a channel 34 centrally therethrough. The channel 34 has an inner diameter slightly larger than the outer diameter of a catheter tube 58 to be inserted therein, thus facilitating the insertion of a catheter tube therein. The gasket 32 includes a frustoconically tapered distal end 36 and a proximal end 38. The lock washer 60 abuts the proximal end 38 of the gasket 32.

Figure 3:
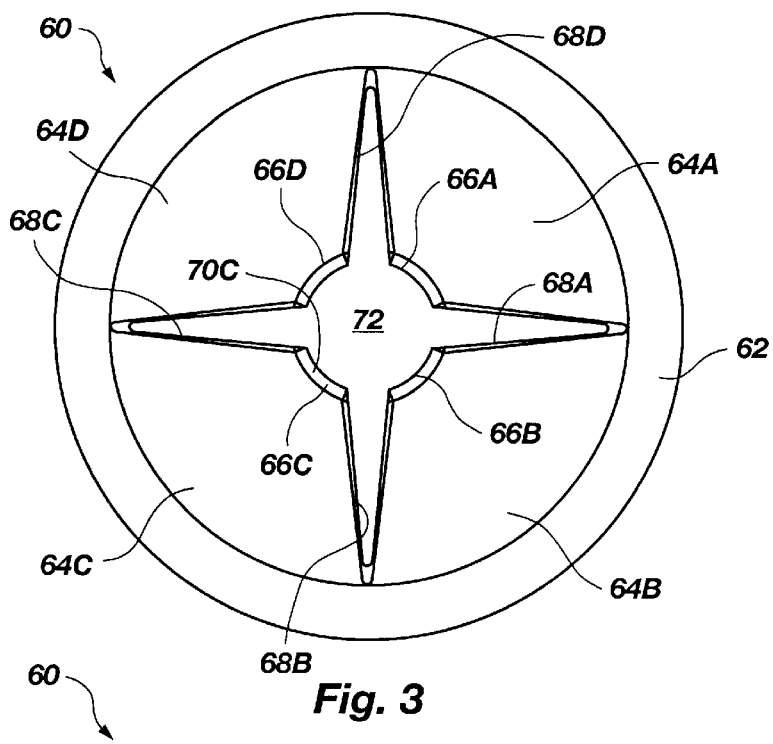
FIG. 3 depicts an enlarged top plan view of the distal end of the embodiment of the preceding two figures, with the lock washer in a relaxed state.
Figure 4:
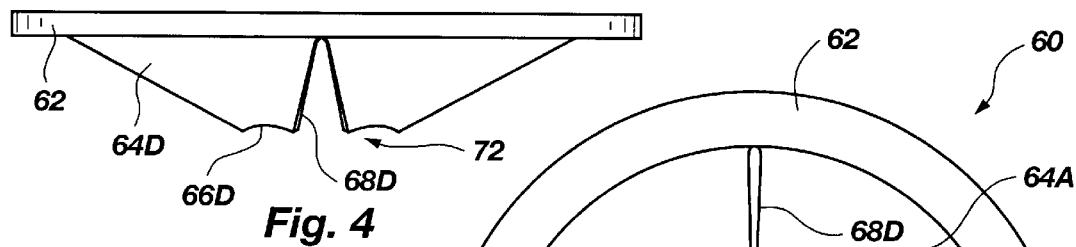
FIG. 4 depicts an enlarged side plan view of the embodiment of the preceding three figures, with the lock washer in a relaxed state.

Referring now to FIGS. 3 and 4, a preferred lock washer 60 includes a support ring 62, which is also referred to as a ring for simplicity, formed or positioned around the perimeter thereof are flared tube engagement flanges 64A, 64B, 64C, 64D extending centrally from the ring 62. A compression slot 68A, 68B, 68C, 68D is defined by the lateral edges of each adjacent pair of tube engagement flanges 64, and is therefore located therebetween. FIGS. 3 and 4 depict the lock washer 60 and its tube engagement flanges 64A, 64B, 64C, 64D in a relaxed, or flared, state. As FIG. 4 illustrates, in the relaxed state of the lock washer 60 and the tube engagement flanges 64A, 64B, 64C, 64D, the tube engagement flanges impart the lock washer with a generally conical shape. Each tube engagement flange 64 is a resilient member that includes a central tip 66A, 66B, 66C, 66D. Preferably, each central tip 66 includes a concave arc 70A, 70B, 70C, 70D. The collective, concave shape of all of the central tips 66A, 66B, 66C, 66D defmes a generally rounded tube receptacle 72 through the center of the lock washer 60. Thus, the central tips 66A, 66B, 66C, 66D, and therefore the tube receptacle 72, are configured to receive a catheter tube 58 (see FIG. 11) inserted through the lock washer 60 while the lock washer is in the relaxed state (see FIGS. 3 and 4), and engage the catheter tube without damaging or closing off the lumen through the same as the lock washer 60 is placed into the engaged state.

Figure 5:
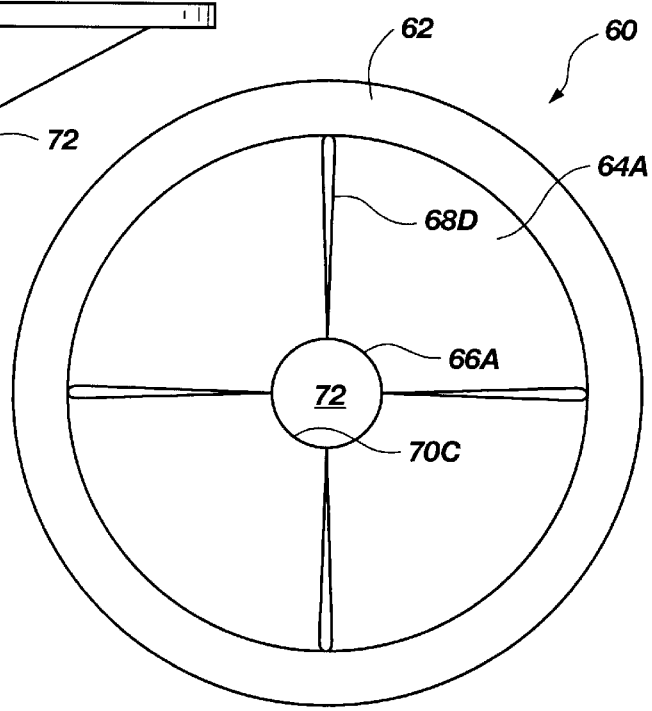
FIG. 5 depicts an enlarged top plan view of the distal end of the embodiment of the preceding four figures, with the lock washer in an engaged state.
Figure 6:
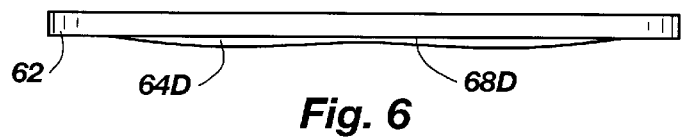
FIG. 6 depicts an enlarged side plan view of the embodiment of the preceding five figures, with the lock washer in an engaged state.

FIGS. 5 and 6 illustrate lock washer 60 and its tube engagement flanges 64 in an engaged state, wherein the tube engagement flanges are flexed towards the center of a plaque in which the ring 62 lies. Consequently, the lateral edges of adjacent tube engagement flanges 64 are forced toward one another and the size of the compression slots 68A, 68B, 68C, 68D is reduced. Additionally, the cross-sectional diameter of tube receptacle 72 is thus decreased, such that it is at least slightly smaller than the outer diameter of a catheter tube 58 insertable therethrough.

Figure 7:
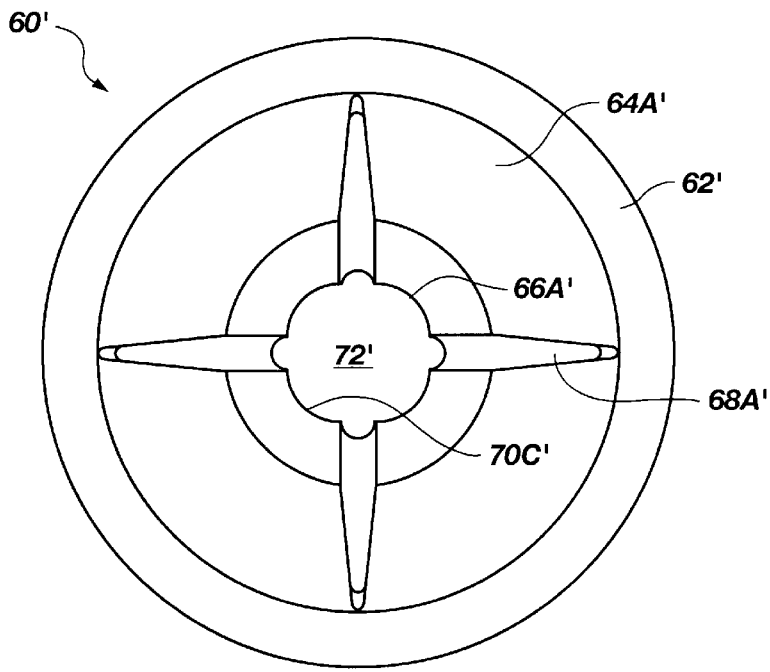
FIG. 7 depicts an enlarged top plan view of the distal end of an alternative embodiment of the lock washer according to the invention.
Figure 8:
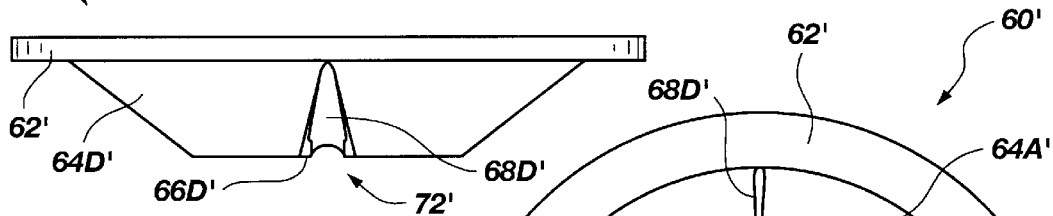
FIG. 8 depicts an enlarged side plan view of the embodiment of the preceding figure, with the lock washer in a relaxed state.
Figure 9:
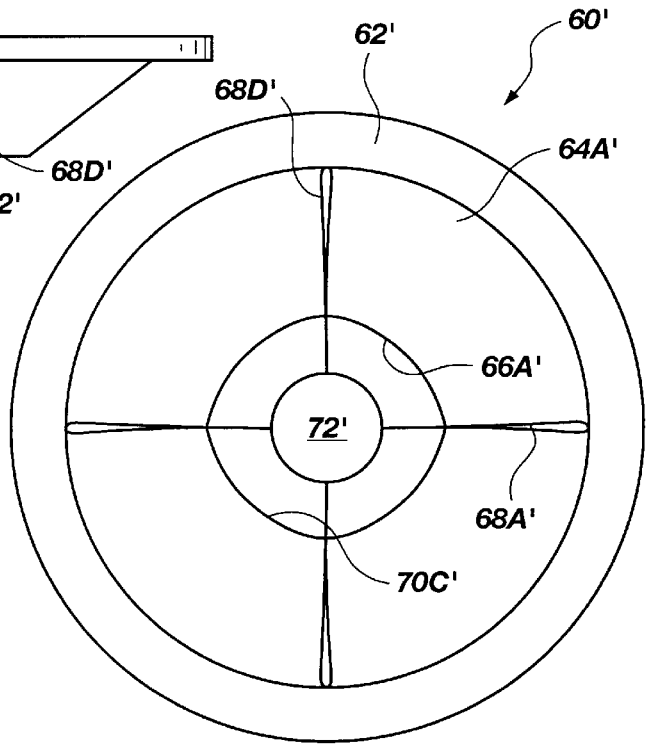
FIG. 9 depicts an enlarged top plan view of the embodiment of the preceding two figures, with the lock washer in an engaged state.
Figure 10:
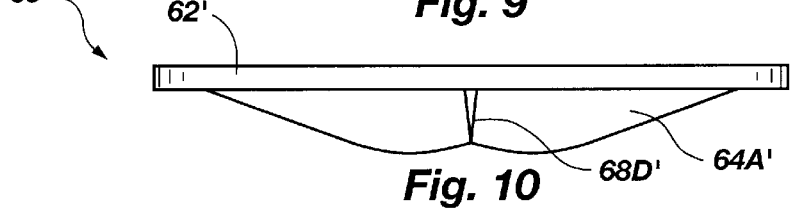
FIG. 10 depicts an enlarged side plan view of the embodiment of the preceding three figures, with the lock washer in an engaged state.

FIGS. 7 through 10 show an alternative embodiment of the lock washer 60', which includes a support ring 62' formed around the perimeter thereof, flared tube engagement flanges 64A', 64B', 64C', 64D' and a thin, flexible, resilient, collapsible web 68'A, 68'B, 68'C, 68'D disposed between and adjoining the lateral edges of adjacent tube engagement flanges 64'. FIGS. 7 and 8 illustrate the lock washer 60' in a relaxed, or flared, state, wherein the lock washer has a generally conical appearance. FIGS. 9 and 10 show the lock washer 60' in an engaged state, wherein the tube engagement flanges 64A', 64B', 64C', 64D' have been flexed toward the ring 62'.

Each tube engagement flange 64A', 64B', 64C', 64D' is a resilient member that includes a central tip 66A', 66B', 66C', 66D'. Preferably, the central tips 66A–D' are collectively configured to receive a catheter tube 58 (see FIG. 11) while the lock washer 60' is in the relaxed state, and engage the catheter tube without damaging or closing off the lumen through the same as the lock washer is compressed into the engaged state.

Webs 68'A, 68'B, 68'C, 68'D are collapsible, resilient elements which facilitate the transition of the tube engagement flanges 64A', 64B', 64C', 64D', and therefore the lock washer 60', from the engaged state to the relaxed state following the release of a transverse load thereon. While the lock washer 60' is in the engaged state, as depicted in FIGS. 9 and 10, the tube engagement flanges 64A', 64B', 64C', 64D' are flexed toward the center of the ring 62', and their lateral edges are therefore forced laterally towards one another. Consequently, webs 68' fold or collapse upon themselves in their engaged state. Additionally, the diameter of tube receptacle 72' is also decreased, such that it is at least slightly smaller than the outer diameter of catheter tube 58 (see FIG. 11) insertable therein in order to engage the catheter tube.

Referring again to FIG. 11, as the insertion member 28 and the center member 24 are interconnected, the lock washer 60 and the gasket 32 are forced together and compressed along their respective transverse axes. Thus, a transverse load is exerted on the lock washer 60, compressing it into the engaged state (illustrated in FIGS. 5 and 6). Therefore, the cross-sectional diameter of tube receptacle is decreased such that the catheter tube 58 extending therethrough is engaged by the compressed the lock washer 60. Similarly, the channel 34 of the gasket 32 is compressed, decreasing its crosssectional diameter such that the gasket will frictionally engage a catheter tube 58 that extends therethrough.

With continued reference to FIG. 11, as an example of the use of the catheter connector 20, a proximal end of a catheter tube 58 that runs from a patient is inserted into the aperture 42 formed through the distal end 54 of the insertion member 28. The catheter tube 58 is then inserted through the channel 34 of the gasket 32, through the tube receptacle 72 of the lock washer 60, and into the lumen 44 of the center member 24. Interconnection of the insertion member 28 and the center member 24 exerts a transverse load on the tube engagement flanges 64A', 64B', 64C', 64D' of the lock washer 60, compressing the lock washer into an engaged position and thereby securing the catheter tube 58 within the catheter connector 20. The engagement of the insertion member 28 and the center member 24 also compresses the gasket 32, decreasing the diameter of the channel 34 so that the gasket frictionally engages the catheter tube 58 extending therethrough. Upon removal of the cap 22 from the center member 24, the lumen of the catheter tube 58 is exposed for connection to another device or for the introduction of substances therein or the removal of fluids therethrough.

Although shown in use as a catheter connector, the invention may also be used to establish and maintain a fluidic connect between other types of tubes.

After being apprised of the devices according to the invention, methods of making them will become readily apparent to those of slill in the art. For instance, a lock washer can be made from a hypoallergenic, firm, resilient plastic material such as acrylonitrile butadiene styrene (ABS), acetyl, nylon, polycarbonate, polyesters, polyethylene, polypropylene, polystyrene, polysulfone, polyurethane, and polyvinyl chloride (PVC). Likewise, a cap, insertion member, and center member may be manufactured from similar materials and by methods which are readily apparent to those of skill in the art. The gasket can be made from a hypoallergenic, collapsible, resilient, low durometer elastomeric material such as a urethane.

Furthermore, the lock washer and connector assembly might otherwise be modified. For instance, in its relaxed state, the lock washer may have a substantially hemispherical appearance. The tube engagement flanges will typically number from three to eight per each lock washer. The connector disclosed herein will work with most types of catheters. The lock washer disclosed herein will work with most Tuohy-Borst catheter connectors. The size of the lock washer and connector will be chosen dependent on the size of the catheter. Typically however, for epidural applications, the lock washer has a diameter of less than about 1 cm and the catheter tube secured thereby has outer diameter of about one mm. As another example, an element other than the described cap, such as a LEUR LOCK™ syringe, may be joined to the connector.

Although the invention has been described with regard to certain preferred embodiments, the scope of the invention is to be defined by the appended claims.

What is claimed is:

1. A catheter connector assembly, comprising:
    a first member including a body having a first lumen therethrough;
    a second member having first and second ends and including a body having a second lumen therethrough, said second member being interconnectable with said first member at said first end; and
    a lock washer disposed within one of said first and said second lumens, said lock washer including a ring, a plurality of compressible tube engagement flanges extending centrally from said ring and defining a tube receptacle, and a collapsible web disposed between adjacent flanges of said tube engagement flanges.

2. The catheter connector assembly of claim 1, wherein said tube engagement flanges are flexible towards the center of a plane, defined by the periphery of said ring.

3. The catheter connector assembly of claim 1 wherein adjacent flanges of said plurality of compressible tube engagement flanges define a compression slot therebetween.

4. The catheter connector assembly of claim 2, wherein, following the release of a compressive load from the periphery of said lock washer, said tube engagement flanges resiliently flex back to a relaxed state.

5. The catheter connector assembly of claim 2, wherein adjacent flanges of said tube engagement flanges defme a compression slot therebetween.

6. The catheter connector assembly of claim 1, wherein, upon interconnection of said first and second members, a diameter of said tube receptacle decreases.

7. The catheter connector assembly of claim 1, further comprising a tube disposed within said tube receptacle.

8. A catheter connector assembly, comprising:
    a first member including a body having a first lumen therethrough;
    a second member having first and second ends and including a body having a second lumen therethrough, said second member being interconnectabl e with sad-first member at said first end; and
    a lock washer disposed within one of said first and said second lumens, said lock washer including a ring, a plurality resilient, compressible tube of engagement flanges extending centrally from said ring and defining a tube receptacle, and a collapsible web disposed between adjacent flanges of said tube engagement flanges.

9. A catheter connector assembly, comprising:
    a first member including a body having a first lumen therethrough;
    a second member having first and second ends and including a body having a second lumen therethrough, said second member being interconnectable with said first member at said first end; and
    a lock washer disposed within one of said first lumen and said second lumen, said lock washer including a ring, a plurality of compressible tube engagement flanges extending centrally from said ring thereby defining a tube receptacle, said plurality of compressible tube engagement flanges flexible toward a plane defined by a periphery of said ring, and a collapsible web disposed between acjacent flanges of said tube engagement flanges.

10. The catheter connector assembly of claim 9, wherein, upon flexion of said adjacent flanges of said tube engagement flanges toward said ring, said web collapses upon itself.

11. The catheter connector assembly of claim 9, wherein, following flexion of said tube engagement flanges, said tube engagement flanges return to a relaxed state and said web re-expands to an original state.

12. The catheter connector assembly of claim 9, wherein each of said compressible tube engagement flanges of said lock washer is resilient.

13. The catheter connector assembly of claim 9, wherein, following the release of a compressive load from the periphery of said lock washer, said tube engagement flanges resiliently flex back to a relaxed state.

14. The catheter connector assembly of claim 9, wherein adjacent flanges of said plurality of compressible tube engagement flanges define a compression slot therebetween.

15. The catheter connector assembly of claim 9, wherein, upon interconnection of said first and second members, a diameter of said tube receptacle decreases.

16. The catheter connector assembly of claim 9, further comprising a tube disposed within said tube receptacle.

\* \* \* \* \*

UNITED STATES PATENT AND TRADEMARK OFFICE
CERTIFICATE OF CORRECTION

PATENT NO : 5,993,437
DATED : November 30, 1999
INVENTOR(S) : Racz

It is certified that error appears in the above-identified patent and that said Letters Patent are hereby corrected as shown below:

On the title page:
In the header, last name of inventor, change "Raoz" to --Racz--; and
In Item [75] "Inventor" change "Raoz" to --Racz--.

In the Specification:

| | | | |
|---|---|---|---|
| Column 2, | line 66, | change "defmed" to --defined--; |
| Column 3, | line 3, | change "locling" to --locking--; |
| Column 3, | line 31, | change "defmes" to --defines--; |
| Column 3, | line 55, | change "defmes" to --defines--; |
| Column 4, | line 53, | change "crosssectional" to --cross-sectional--; and |
| Column 5, | line 16, | change "slill" to --skill--. |

In the Claims:

| | | | |
|---|---|---|---|
| Claim 5, | Column 6, | line 4, | change "defme" to --define--; |
| Claim 8, | Column 6, | line 16, | change "interconnectabl e" to --interconnectable-- and change "sad-" to --said--; |
| Claim 8, | Column 6, | line 20, | after "plurality" insert --of-- and after "tube" delete "of"; and |
| Claim 9, | Column 6, | line 39, | change "acjacent" to --adjacent--. |

Signed and Sealed this

Twenty-second Day of May, 2001

*Attest:*

NICHOLAS P. GODICI

*Attesting Officer*  *Acting Director of the United States Patent and Trademark Office*